United States Patent
Suzuki et al.

(10) Patent No.: US 6,391,013 B1
(45) Date of Patent: May 21, 2002

(54) ABSORBENT ARTICLE AND METHOD OF MANUFACTURING THE SAME

(75) Inventors: Migaku Suzuki, Kanagawa; Hiroaki Fukui, Saitama, both of (JP)

(73) Assignee: Japan Absorbent Technology Institute (JP)

( * ) Notice: Subject to any disclaimer, the term of this patent is extended or adjusted under 35 U.S.C. 154(b) by 1253 days.

(21) Appl. No.: 08/770,676

(22) Filed: Dec. 20, 1996

Related U.S. Application Data

(63) Continuation of application No. 08/501,287, filed on Jul. 12, 1995, now abandoned, which is a continuation of application No. 08/243,777, filed on May 17, 1994, now abandoned.

(30) Foreign Application Priority Data

May 26, 1993 (JP) .............................................. 5-145361

(51) Int. Cl.$^7$ ........................... A61F 13/15; A61F 13/20
(52) U.S. Cl. ........................... 604/385.27; 604/385.19; 604/385.29; 604/396; 156/161; 156/164; 156/229; 156/256; 156/264
(58) Field of Search ................................. 156/161, 163, 156/164, 229, 256, 264; 604/385.1, 385.2, 393–399, 385.19, 385.24–385.3

(56) References Cited

U.S. PATENT DOCUMENTS 4,892,536 A * 1/1990 DesMarais et al.
5,147,487 A * 9/1992 Nomura et al. .......... 604/385.2
5,171,239 A * 12/1992 Igaue et al.
5,213,645 A * 5/1993 Nomura et al.
5,340,424 A * 8/1994 Matsushita ................ 604/385.2

FOREIGN PATENT DOCUMENTS

| EP | 0048011 | * | 3/1982 | |
| JP | 428364 | * | 1/1992 | |
| JP | 542180 | * | 2/1993 | |
| JP | 576566 | * | 3/1993 | |
| JP | 6197925 | * | 7/1994 | .................. 604/396 |
| JP | 626160 | * | 11/1994 | .................. 604/396 |
| JP | 626161 | * | 11/1994 | .................. 604/396 |

* cited by examiner

Primary Examiner—John G. Weiss
Assistant Examiner—K. M. Reichle
(74) Attorney, Agent, or Firm—Hunton & Williams; Christopher C. Campbell

(57) ABSTRACT

An absorbent article having a main body which includes a backsheet formed of a liquid impermeable sheet, a topsheet formed of a liquid permeable sheet, an absorbent core interposed between the backsheet and the topsheet, and leg gathers disposed along leg holes. Two sets of elastic members are, in a stretched state, bonded to a non-woven fabric along the leg holes. Each set of elastic members is not bonded to the non-woven fabric in a region which traverses a crotch region to extend from one of the leg holes to the other, and is cut in the non-bonded region so that the elastic members snap back toward crossing points where the two sets of the elastic members meet to form tails.

7 Claims, 4 Drawing Sheets

ABSORBENT ARTICLE AND METHOD OF MANUFACTURING THE SAME

This application is a continuation of application Ser. No. 08/501,287, filed Jul. 12, 1995 which was a continuation of application Ser. No. 08/243,777, filed May 17, 1994, both now abandoned.

FIELD OF THE INVENTION

The present invention relates to a pant-type absorbent article (such as those often referred to as "tapeless-type" or "training pant type") which includes a pair of leg holes for leg insertion, and a waist hole for encircling a waist portion of a body. The present invention further relates to a method for manufacturing such an absorbent article. The absorbent article of this type may be used for infant and adult diapers, feminine sanitary products and the like.

SUMMARY OF THE INVENTION

Absorbent articles, particularly infant and adult diapers, have recently gained increased acceptance from consumers for their advantageous characteristics of stability during use and reduced leakage.

In order for tapeless absorbent articles to fully exhibit their advantageous characteristics, they need to fit snugly to a user's body, particularly at leg hole portions thereof. To this end, such tapeless absorbent articles have elastically stretchable ruffles or leg gathers, as they are generally called, along peripheries of the leg holes.

One example of such tapeless absorbent articles with leg gathers is disclosed in Japanese Patent Application No. 3-195558. Two sets of elastic members are attached along the peripheries of the leg holes to form leg gathers. Each set of elastic members extends along one leg hole from a front end of the leg hole to a midpoint of the leg hole, and continuously extends transversely of a central region (crotch region) of the article to a midpoint of the other leg hole to form a cross-over portion. From the midpoint of the other leg hole, each set of elastic members further extends therealong to a rear end of the other leg hole. Those two sets of elastic members are arranged so as to define a somewhat X-shaped configuration.

Such arrangement of the elastic members advantageously facilitates a continuous manufacturing process of the absorbent articles. Specifically, a liquid impermeable sheet in a continuous web form is continuously transported in one direction. Continuous elastic strands are fed onto the sheet in a sinusoidal configuration for securement thereto. The resultant combination is cut at a predetermined interval to form a composite back sheet incorporating the elastic members secured thereto.

The elastic members arranged along peripheries of the leg holes in the aforementioned, conventional tapeless absorbent article function to form leg gathers therealong. However, the elastic members extending transversely of the crotch region not only are non-functional waste material but cause the absorbent article to deform at the crotch region when they elastically contract.

An attempt to remedy such disadvantages has been made by adjusting a stretching or contracting rate of the elastic members to be lower at the crotch region than along the leg holes. However, it complicates a manufacturing process, and lowers productivity to intermittently change the stretching rate of the elastic members during the continuous manufacturing process wherein the continuous elastic members are fed along predetermined lines on a web for securement thereto. The elastic members tend to impair flexibility and comfort to a wearer during use at the crotch region of the absorbent article where it is desired to be sufficiently flexible to provide comfort to the wearer during use. Furthermore, added elastic material for the elastic members is required at the cross-over region when they are secured to the back sheet at the lower stretching rate. This results in an increased material use as those elastic members at the cross-over region are not necessary.

The two sets of elastic members secured to the back sheet create bundle-like bunches at the crotch region of the absorbent article, which results in the article having a poor appearance.

It is an object of the present invention to provide an improved absorbent article which is capable of eliminating the above-described disadvantages that conventional articles possess, so that any undesirable deformation of the crotch region due to the contracting force of the elastic members is avoided, and flexibility thereat is insured.

It is an other object of the present invention to provide a method for manufacturing such an absorbent article.

In accordance with the present invention, there is provided an absorbent article which is provided with a main body having a waist hole and a pair of leg holes. The main body comprises a liquid impermeable back sheet, a liquid permeable top sheet and an absorbent core interposed between the back sheet and the top sheet. The absorbent article is further provided with a waist gather disposed along the waist hole, and a leg gather disposed along each of the pair of leg holes.

The top sheet may include two layers of sheet materials, and two sets of elastic members interposed between the two sheets of material to form a composite sheet. The first of the two sets of elastic members extend along a periphery of a first leg hole from a front end thereof to a midpoint thereof, and continuously extend transversely to a midpoint of a second leg hole to form a cross-over portion having a central section spaced inwardly from and intermediate the leg holes. From the midpoint of the second leg hole, the first set of elastic members extends to the front end of the second leg hole. The second of the two sets of elastic members extends along a periphery of the first leg hole from a rear end thereof to a mid-point thereof, and continuously extends transversely to a mid-point of the second leg hole to form a cross-over portion having a central section spaced inwardly from and intermediate the leg holes. From the mid-point of the second leg hole the second set of elastic members extends to the rear end of the second leg hole, so that the two sets of elastic members are arranged to define an X-shaped configuration. The two sets of the elastic members are secured in a stretched state to the sheet materials along areas that extend along the peripheries of the leg holes. The central sections of the cross-over portions thereof are not secured to the sheet materials, and are separated so that they snap back toward cross portions of the two sets of the elastic members to define tail portions extending from the cross portions.

As such, the absorbent article in accordance with the present-invention has the elastic members extending around leg holes to form leg gathers. The elastic members do not cross the crotch region of the article. Accordingly, the absorbent article provides a snug fit and comfort to the wearer during use, with its leg gathers effectively preventing leakage from the article. The leg elastic members are not secured to the back sheet, so that the absorbent article provides a good appearance.

In one embodiment of the present invention, the top sheet has a through aperture in the crotch region of the absorbent article. The aperture serves as an inlet void of a pocket for communicating urine and fecal material into the pocket defined between the top sheet and the back sheet. This provides comfort to the wearer during use.

The present invention further provides a method for manufacturing a tapeless absorbent article which comprises a main body having a waist hole and a pair of leg holes and comprising a liquid permeable top sheet, a liquid impermeable back sheet and an absorbent core interposed between the top sheet and the back sheet, a waist gather disposed along the waist hole, and a leg gather disposed along each of the leg holes.

Two sets of elastic members in their stretched conditions are positioned, between two sheets of material in elongated web forms, in overlapping sinusoidal configurations with an inverted phase relation to each other, so that the two sets of elastic members define a number of elongated oblong areas therebetween. The elastic members are bonded to the sheet material in alternate ones of the oblong areas, and are cut or separated in the oblong areas in which they are not secured so that they snap back toward crossing, or intersecting, portions thereof.

The top sheet is combined with the back sheet prior to bi-folding of the resultant combination along a transverse center line. The bi-folded resultant combination is severed along predetermined cutting lines.

The present method can advantageously provide a highly productive process which is capable of securing elastic members to sheet materials without varying the feed rate of the sheet materials.

One embodiment of the present invention will be explained hereinafter with reference to the drawings.

DESCRIPTION OF THE PREFERRED EMBODIMENT

Figure 1:
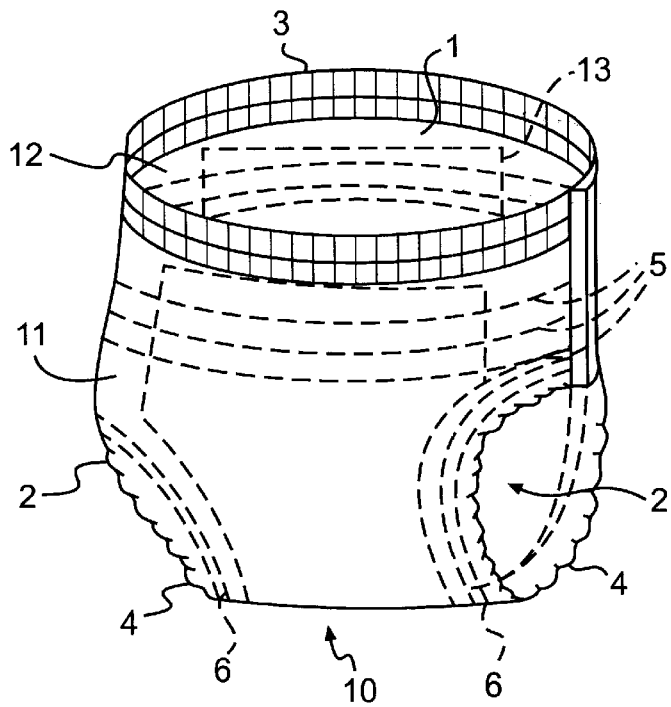
FIG. 1 is a perspective view illustrating one embodiment of an absorbent article in accordance with the present invention.
Figure 2:
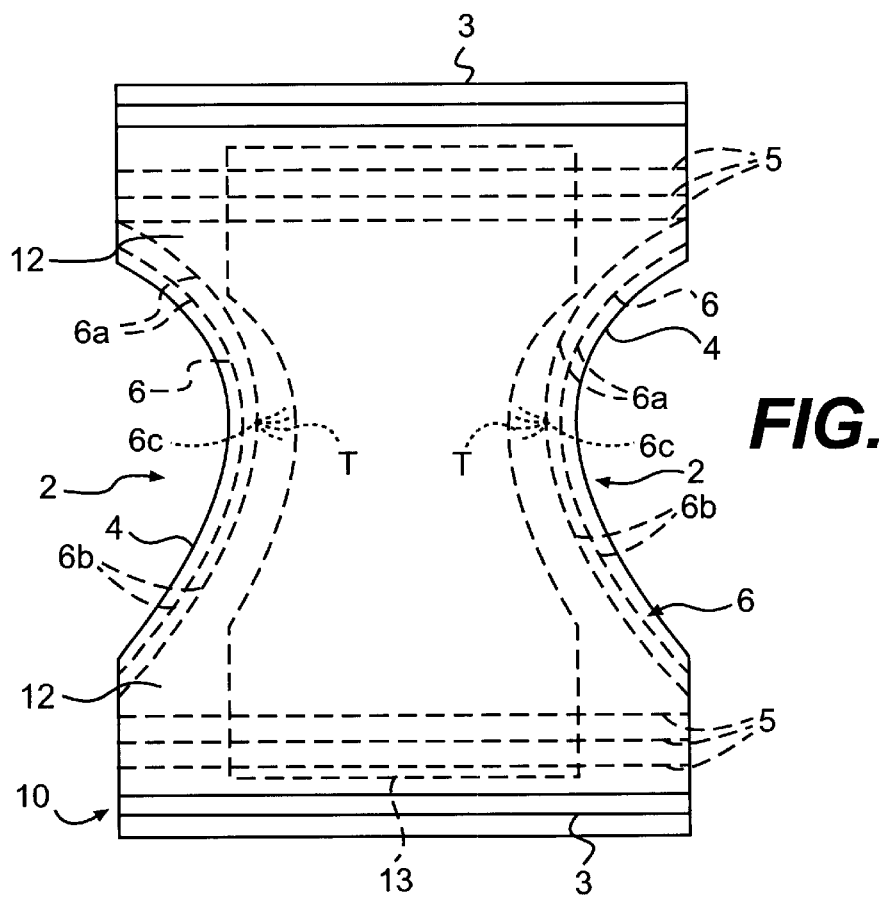
FIG. 2 is a plan view of the absorbent article of FIG. 1 prior to bi-folding and securing the respective side panels thereof.

FIG. 1 is a perspective view illustrating one embodiment of an absorbent article in accordance with the present invention. FIG. 2 is a developed plan view illustrating the absorbent article of FIG. 1 prior to bi-folding and sealing the respective side panels thereof to each other.

The absorbent article as illustrated in FIG. 1 comprises a main body 10 which has a waist hole 1 and a pair of leg holes 2. The main body 10 includes a waist gather 3 disposed along the periphery of the waist hole 1, and a leg gather 4 disposed along the periphery of each of the leg holes 2. The leg gather 4 is formed by contracting forces of a number of elastic members 6 incorporated therein. A reference numeral 5 illustrates elastic members optionally provided for an improved fit of the main body to a waist portion of a wearer.

The main body 10 comprises a back sheet 11 formed of liquid impermeable material, and a top sheet 12 formed of liquid permeable material, preferably hydrophobic material, and an absorbent core 13 interposed therebetween.

In the illustrated embodiment, the elastic members 6 extend inwardly of, adjacent to, and along each of right and left, contoured edges of the absorbent article which form the leg holes, or openings, as shown in FIG. 2. One of the important features of the present invention is that the elastic members 6 are positioned between the two sheets of material, such as non-woven fabrics, which form the top sheet. Another important feature is that each set of elastic members is divided, or separated, at their longitudinal intermediate portions to form two portions 6a, 6b, and respective ends of the two portions 6a, 6b snap back toward the crossing point, or intersection, 6c where they meet to form tails T.

A method for manufacturing the absorbent article as explained above will be now described.

Figure 3:
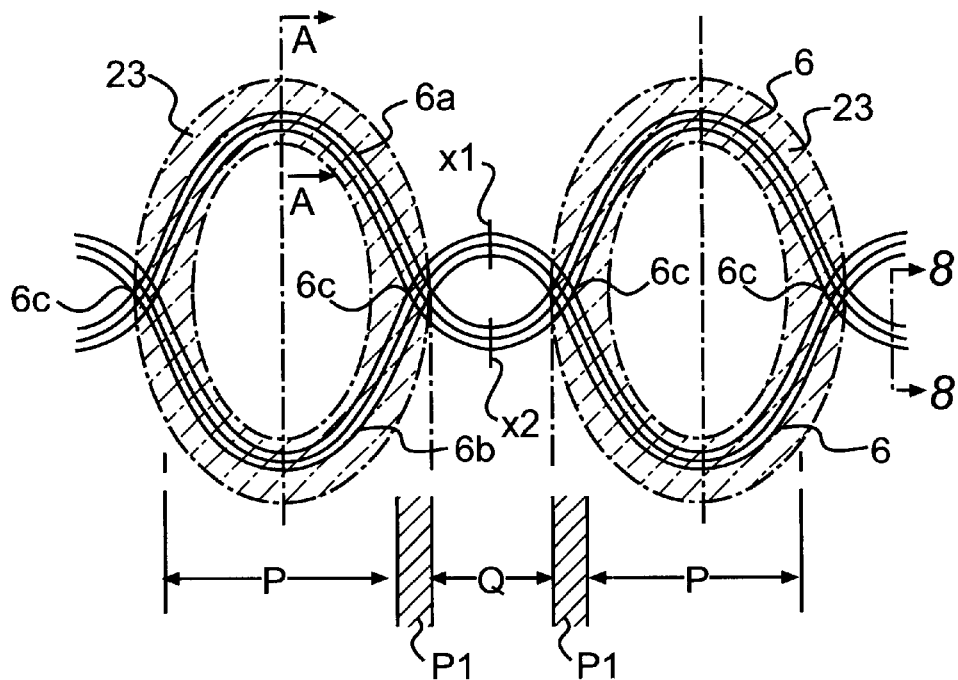
FIG. 3 is an explanatory view illustrating an intermediate product during the process of manufacturing a top sheet for use in an absorbent article of the present invention.
Figure 4A:
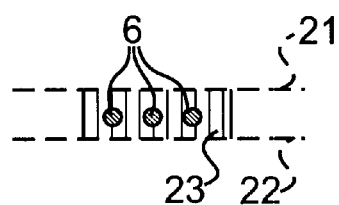
FIG. 4A is a fragmentary cross-sectional view taken along a line A—A of FIG. 3.
Figure 4B:
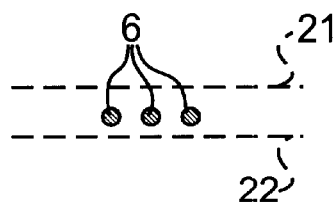
FIG. 4B is a cross-sectional view taken along a line B—B of FIG. 3.

In FIGS. 3, 4A and 4B, the two sets of elastic members 6 are positioned between two sheets of material, such as two non-woven sheets of fabric 21, 22, and are arranged in overlapping, intersecting, sinusoidal configurations with an inverted phase relation to each other, so that they define a number of oblong areas therebetween. The elastic members 6 are disposed in opposed sinusoidal configurations 6a, 6b, such that they have outwardly curved portions in the region designated P which are relatively widely spaced from each other and inwardly curved portions in region Q where they are more closely spaced to each other. They intersect each other at cross, or intersecting, portions noted at 6c. The more closely spaced inwardly curved portions are disposed in and have central sections in what will become the crotch region of the article. These elastic members 6 are positioned in a uniformly, properly stretched, state and are bonded to the non-woven fabrics in alternate ones of the oblong areas. A reference numeral 23 illustrates bonding, denoted by shading, where the bonding is provided between the two non-woven fabrics 21, 22, and also between the elastic members 6 and the non-woven fabrics by appropriate bonding means, such as by applying heat and compression, or by the application of adhesives. Reference P indicates bonding regions where the elastic members 6 are bonded to the non-woven fabrics, and reference Q indicates a non-bonding region where the elastic members 6 are not bonded to the non-woven fabrics. Reference P1 indicates the region of intersection between elastic members 6 which also is a bonding region. The two sets of the elastic members 6 extend along the peripheries of the area that will become leg holes 2 in the bonding regions P, P1 and extend between the adjacent leg holes in the non-bonding regions Q to form cross-over portions. The cross-over portions have central sections spaced inwardly from and intermediate cross, or intersecting, portions 6c.

In the illustrated embodiment, the amplitude of the sinusoidal configuration that each set of the elastic members 6 describes is designed to be greater in the bonding region P than in the non-bonding region Q. This design is intended to decrease length dimensions of the elastic members 6 extending over the non-bonding region Q, so that material cost therefor is reduced, and also length dimensions of the tails T that consequently remain after the division, or severing, of the elastic members 6 over the region Q are effectively decreased.

Figure 5:
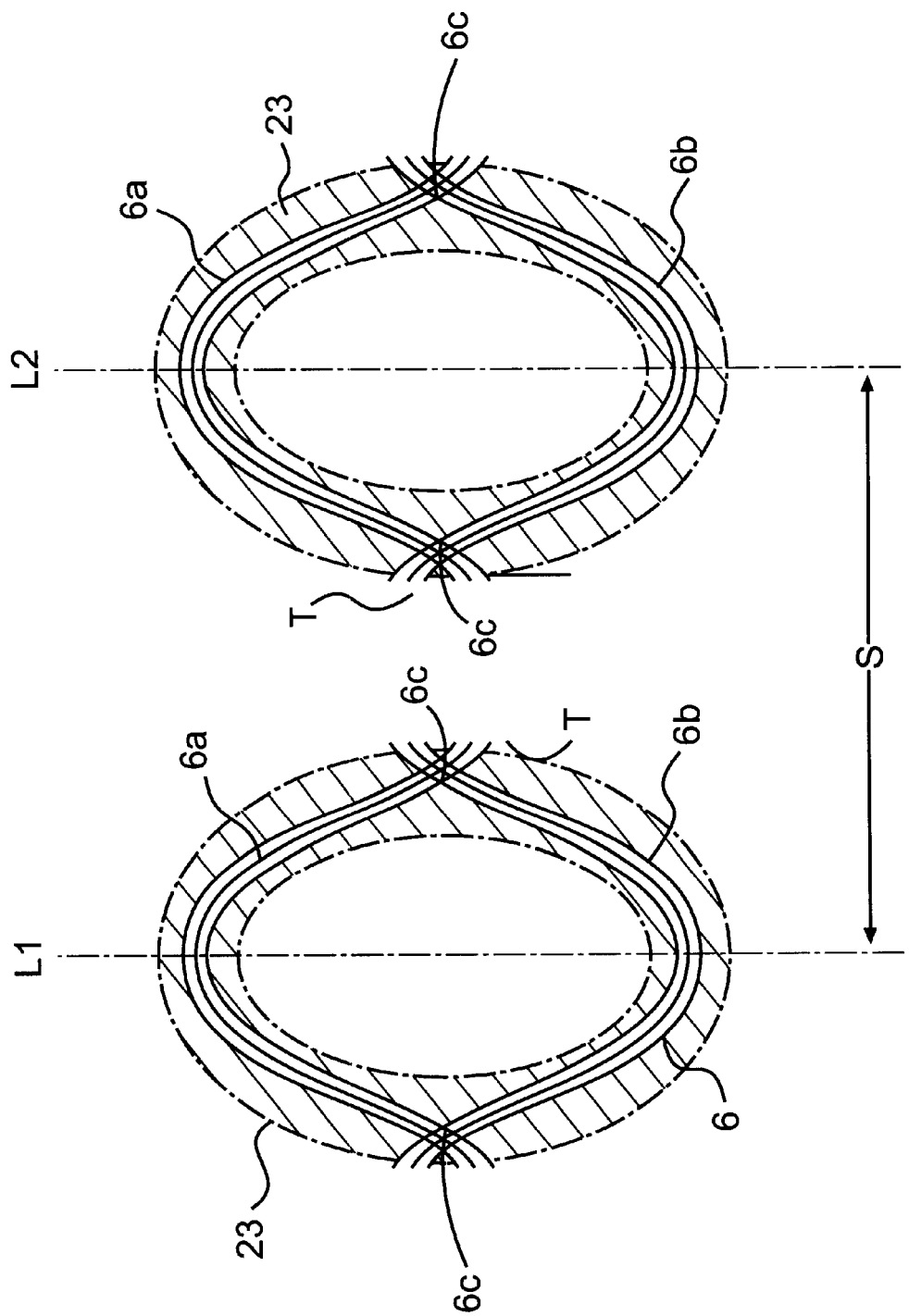
FIG. 5 is an explanatory view illustrating an intermediate product with portions of elastic members separated.

The elastic members 6 as partially secured between the non-woven fabrics 21, 22 are cut out, or severed, along cutting lines X1, X2 in the central sections of the cross-over portions in the non-bonding region Q, together with the non-woven fabrics 21, 22. The elastic members 6 are not bonded to the non-woven fabrics 21, 22 over the non-bonding regions Q, so that the cutting allows the elastic members 6 in a stretched state to elastically contract due to elastic recovery thereof, and form short tails T, as illustrated in FIG. 5, adjacent intersections 6c.

When region S is cut out along lines L1, L2, a top sheet is obtained which comprises respective halves of the two adjacent, semi-oblong bonding regions P, and the non-bonding region Q located therebetween.

The cutting of the elastic members simultaneously may cut the non-woven fabrics which enclose the elastic members to form slits therein. Those slits however do not create any adverse results since they are formed in the liquid permeable top sheet.

The elastic members 6 secured to the non-woven fabrics 21, 22 elastically contract due to elastic recovery thereof to form gathers in the region P of the top sheet like conventional articles. The non-bonded portions of elastic members 6 remain as tails T in the non-bonding region Q (corresponding to the crotch region of the absorbent article) located between the two adjacent bonding regions P. As the tails T are not secured to the non-woven fabrics in the region Q, those non-woven fabrics retain their original flexibility and softness. Accordingly, the top sheet provides an excellent conformity to undulation of a wearer's body.

In the embodiment as illustrated in FIG. 3, the amplitude of the sinusoidal configuration that each set of the elastic members 6 describe is selected to be greater in the bonding region P than in the non-bonding region Q. This design permits the quantity and thus the material cost of the elastic members 6 which is not desired in the crotch region to be reduced, and the length dimensions of the tails T that remain after divisions thereof to be decreased.

For the same reason, the stretching rate of the elastic members 6 in the non-bonding regions Q may be increased. For instance, the stretching rate in the non-bonding regions Q is set to about 200% when that in the bonding regions P is selected to be about 100%. Such adjustment of the stretching rate may be made by periodically varying the feed rate of the elastic members.

In another embodiment of the present invention, the cutting of the elastic members 6 simultaneously forms a through aperture in the top sheet.

FIGS. 6A, 6B, 6C, 6D illustrate top sheets 12 respectively having through apertures 30 of various sizes and shapes which cut out both the elastic members 6 and the non-woven fabrics 21, 22.

Figure 6A:
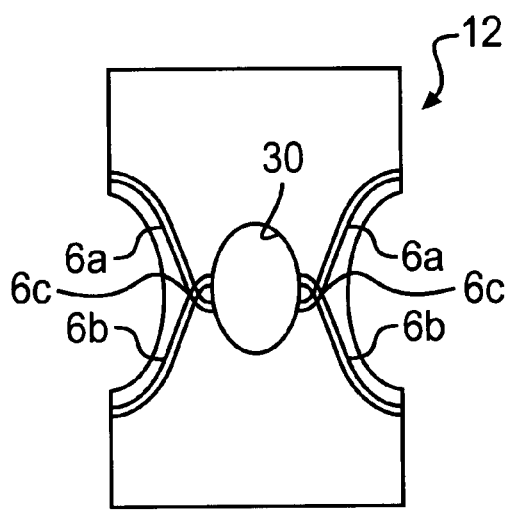
FIGS. 6A, 6B, 6C, 6D respectively illustrate plan views of various embodiments of top sheets for use in an absorbent article in accordance with the present invention.
Figure 6C:
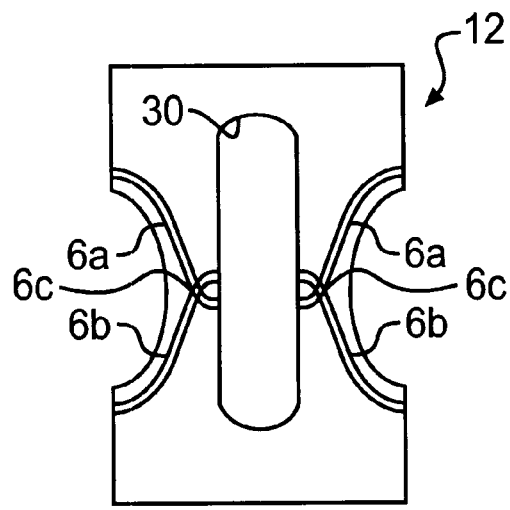
Figure 6B:
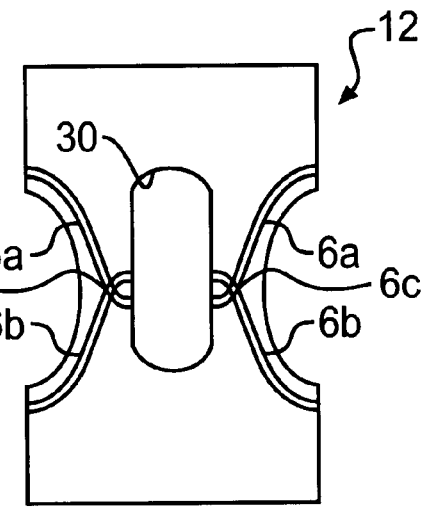
Figure 6D:
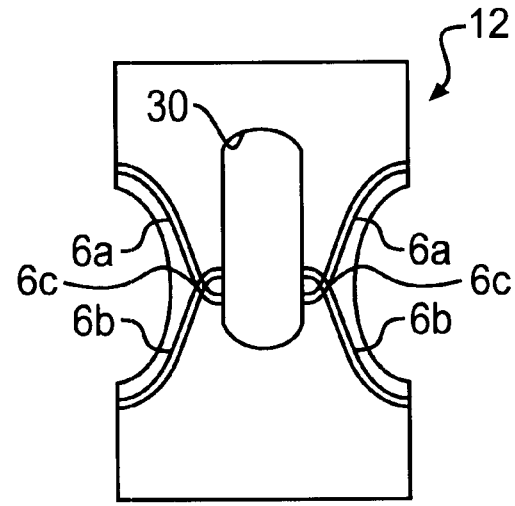

In FIG. 6A, the cutting is applied in a region located between the two adjacent crossing, or intersecting, portions 6c where the two portions 6a, 6b of the elastic members meet to form leg gathers 4, so that the two non-woven fabrics 21, 22 and the elastic members 6 are simultaneously cut out to form an oblong or elongated circular through aperture 30. In FIG. 6B, the top sheet is illustrated to have the through aperture 30 which is more elongated longitudinally than the aperture 30 of FIG. 6A. The through aperture 30 of FIG. 6C is more elongated longitudinally than the aperture 30 of FIG. 6B. The through aperture 30 of FIG. 6D is longitudinally offset toward a front or rear end of the top sheet.

The top sheet with the through aperture 30 is then combined with the back sheet to form an absorbent article. When the absorbent article is applied to a wearer, the through aperture 30 is designed to be placed in facing relation to a crotch region of the wearer. Accordingly, the through aperture 30 serves to allow urine and fecal materials to pass into a space defined between the top sheet 12 and the back sheet 11. This helps provide comfort to the wearer during prolonged use.

Although each of the two sheets of material of the top sheet is described above as comprising a non-woven fabric, the one sheet material positioned in facing relation to the back sheet may alternatively comprise a synthetic resin film, or the like when the through aperture 30 is formed, for example as illustrated in FIGS. 6A through 6D.

After the top sheet and back sheet are combined material inside the bonded oblong regions of sections P are removed to provide cut-outs to form leg holes in the formed garment. Cuts are made along lines L1, L2 to sever the garment in region S from contiguous garments in the production line. The severed garment then is bi-folded about its transverse center line to the configuration shown in FIG. 1 and side seams are sealed at opposite sides of the waist region to form a garment with the defined waist hole and leg holes.

As explained above, in accordance with the absorbent article of the present invention, the elastic members for forming leg gathers are positioned and extend substantially continuously adjacent and along the leg holes. Since the elastic members actually intersect and cross over each other adjacent the leg holes they provide elasticized leg gathers extending substantially continously along the leg holes to inhibit leakage. Only small parts thereof remain as tails in the crotch region where such elastic members are not required. Accordingly, the absorbent article of the present invention can provide excellent flexibility, a snug fit and comfort to the wearer during use, while effectively preventing leakage from the leg gathers. Furthermore, as the elastic members for forming the leg gathers are not bonded directly to the back sheet, the elastic members are not viewed or observed from outside the absorbent article. This helps provide the article with a better appearance, particularly in its crotch region.

When the through aperture is formed in the crotch region of the top sheet, the article can provide comfort to the wearer as the aperture serves as an inlet of a pocket for communicating urine and fecal material to the pocket. In accordance with the present method, such absorbent articles can be readily manufactured in continuous processes, with a reduced material cost of the elastic members.

What is claimed is:

1. An absorbent article comprising:
   a main body having a waist hole and first and second leg holes each having a front end and a rear end, said main body comprising a top sheet for facing toward a wearer's body, a back sheet disposed outwardly of the top sheet, and an absorbent core interposed between the top sheet and the back sheet, said top sheet, back sheet and absorbent core secured together to form an integral absorbent article;
   a waist gather disposed along the waist hole;
   said top sheet comprising dual-layered sheet material, and two sets of elastic members interposed between the dual sheet material to provide a leg gather disposed along each of the leg holes, with a first set of the two sets of elastic members extending along a periphery of the first leg hole from the front end thereof to a midpoint thereof, and extending continuously therefrom to a midpoint of the second leg hole to form a crossover portion having a central section intermediate said leg holes, and further extending to the front end of the second leg hole, a second set of the two sets of elastic members extending along a periphery of the first leg hole from the rear end thereof to the midpoint thereof, crossing said first set adjacent to the first leg hole at a first intersecting portion, extending continuously therefrom to the midpoint of the second leg hole to form a crossover portion having a central section intermediate said leg holes, crossing said first set adjacent the second leg hole at a second intersecting portion, and further extending to the rear end of the second leg hole, so that the two sets of elastic members are arranged to define an X-shaped configuration, said elastic members being bonded in a stretched state to said sheet materials along areas that extend along the leg holes so as to exclude the central sections of the crossover portions from the bonding, said elastic members being cut at the central sections of the crossover portions so that they can snap back toward said first and second intersecting portions to define unstretched tail portions extending from the cross portions.

2. The absorbent article of claim 1, wherein said dual-layered sheet material and the elastic members and cut out together in the central sections of the crossover portions to form an aperture in said top sheet.

3. The absorbent article of claim 1 wherein said top sheet comprises a non-woven fabric disposed to face toward the wearer's body, and a synthetic resin film disposed to face toward the back sheet.

4. A method of manufacturing an absorbent article which comprises a main body having a waist hole and pair of leg holes with a crotch region between said leg holes and comprising a liquid-permeable top sheet, a liquid-impermeable back sheet and an absorbent core interposed between the top sheet and the back sheet, a waist gather disposed along the waist hole, and a leg gather disposed along each of the leg holes, the method comprising the steps of:

forming the top sheet by positioning, between two sheets of material in elongated web form, a pair of elastic members in overlapping sinusoidal configurations with an inverted phase relation to each other so that they define a plurality of elongated oblong areas therebetween, bonding the elastic members to the sheet material in alternate ones of the oblong areas, with the elastic members in intermediate oblong areas between said alternate ones of the oblong areas not being bonded to the sheet material except in regions where said elastic members intersect in said overlapping sinusoidal configuration, cutting the elastic members in the intermediate oblong areas in which they are not bonded allowing them to snap back toward bonded areas thereof;

combining said top sheet with the back sheet; and severing the resultant combination along predetermined cutting lines to define leg holes whereby the elastic members bonded to the sheet material form leg gathers extending continuously along said leg holes.

5. The method of claim 4, wherein said alternate ones of the oblong areas and the intermediate oblong areas comprise alternating large and small oblong areas, respectively, and the elastic members are bonded to the sheet material in portions having the large areas.

6. The method of claim 4, wherein in said severing step the combination is severed along cutting lines whereby an intermediate oblong area between said alternate ones of the oblong areas which is not bonded occupies the crotch region and the bonded areas are adjacent the leg holes.

7. The method of claim 4, wherein the top sheet is cut out in the region of the intermediate oblong areas defined by said elastic members to form apertures in the top sheet.

* * * * *